US 6,562,294 B1

(12) United States Patent
Smith

(10) Patent No.: US 6,562,294 B1
(45) Date of Patent: May 13, 2003

(54) APPARATUS AND METHOD FOR DISSEMINATING AN AIR MODIFYING AGENT

(75) Inventor: Nigel Peter Smith, Wellington (GB)

(73) Assignee: Globol Chemicals (UK) Limited (GB)

( * ) Notice: Subject to any disclaimer, the term of this patent is extended or adjusted under 35 U.S.C. 154(b) by 0 days.

(21) Appl. No.: 09/561,328

(22) Filed: Apr. 28, 2000

(30) Foreign Application Priority Data

Oct. 31, 1997 (GB) .............................. 9723053

(51) Int. Cl.[7] .............................. A61L 9/00; A62B 7/08
(52) U.S. Cl. .......................... 422/5; 422/122; 422/126; 422/305; 422/306
(58) Field of Search ............................. 422/4, 5, 125, 422/126, 305, 306, 1, 122

(56) References Cited

U.S. PATENT DOCUMENTS

| 2,254,906 A | | 9/1941 | Petrulis ........................ 422/117 |
| 5,669,767 A | * | 9/1997 | Bureau et al. ............... 431/320 |
| 5,744,106 A | * | 4/1998 | Eagle .......................... 422/306 |
| 5,840,246 A | | 11/1998 | Hammons et al. ............. 422/4 |
| 5,840,257 A | * | 11/1998 | Bureau et al. ............... 422/125 |

FOREIGN PATENT DOCUMENTS

| FR | 2483782 | 12/1981 |
| FR | 2687408 | 8/1993 |
| FR | 2759591 | 8/1998 |
| NL | 1006055 | 11/1998 |

* cited by examiner

*Primary Examiner*—Robert J. Warden, Sr.
*Assistant Examiner*—Monzer R. Chorbaji
(74) *Attorney, Agent, or Firm*—Nixon Peabody LLP

(57) ABSTRACT

An apparatus and method are provided, which enable an air modifying agent such as an insecticide, pesticide, insect repellant, fragrance, perfume etc. to be disseminated into an atmosphere. The air modifying agent is entrained in a flammable liquid carrier (2) which is less volative than the agent, which is held in a container (1). A wick (3) draws the agent/carrier (2) up to an igniting station provided at the rim (5) of a metal collar (4) which closely encircles the wick (3). The collar (4) is provided with a pair of diametrically opposed elongate slots (8), which expose part of the wick (3) to the atmosphere and thereby provide a vaporisation station spaced below the igniting station and disposed in the path of the flammable liquid carrier. In use, heat from a flame (6) passes along the collar (4) and warms the wick (3) in the vaporisation station, thereby assisting the preferential evaporation of the air modifying agent from the vaporisation station, away from the flammable liquid carrier prior to the latter's combustion in the flame (6). An angled deflecting plate (10) is also provided to deflect the evaporated air modifying agent away from the flame (arrow A).

33 Claims, 3 Drawing Sheets

Figure 1:
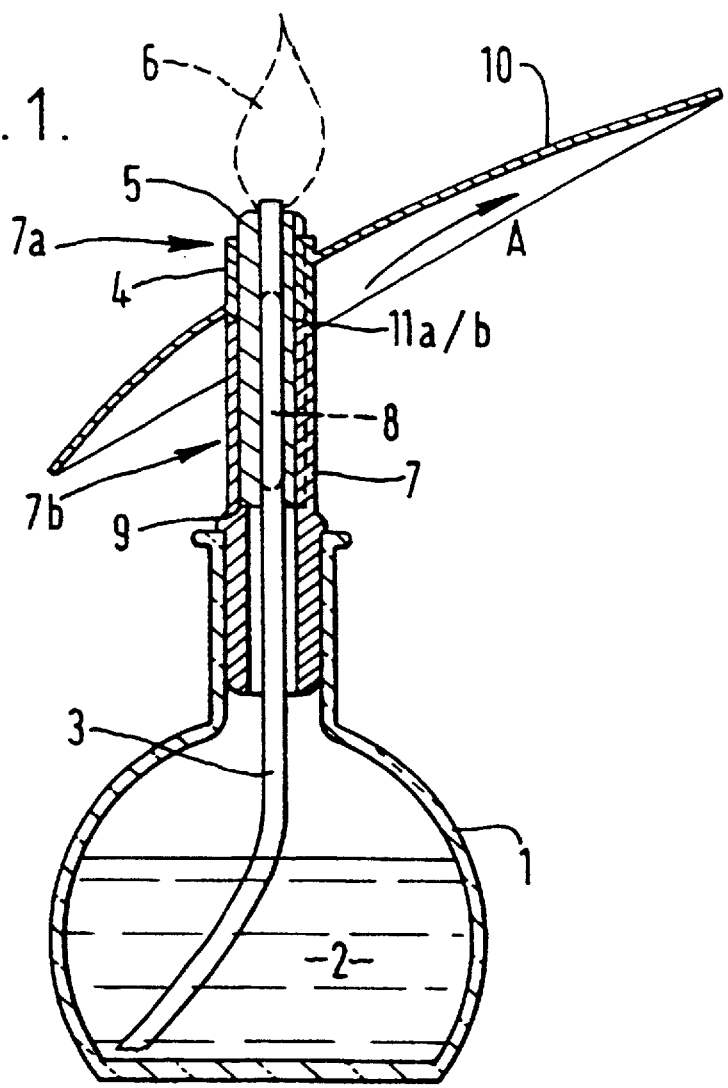
Figure 2:
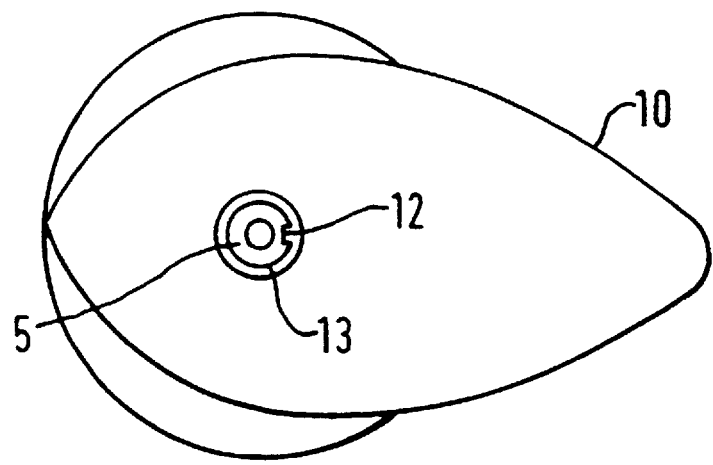

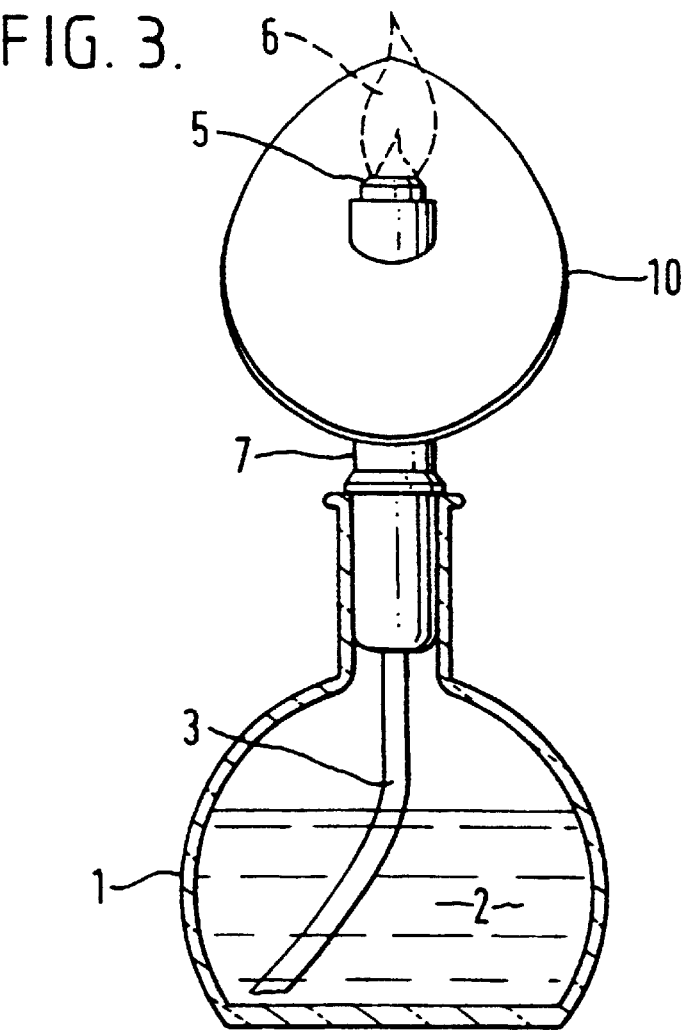
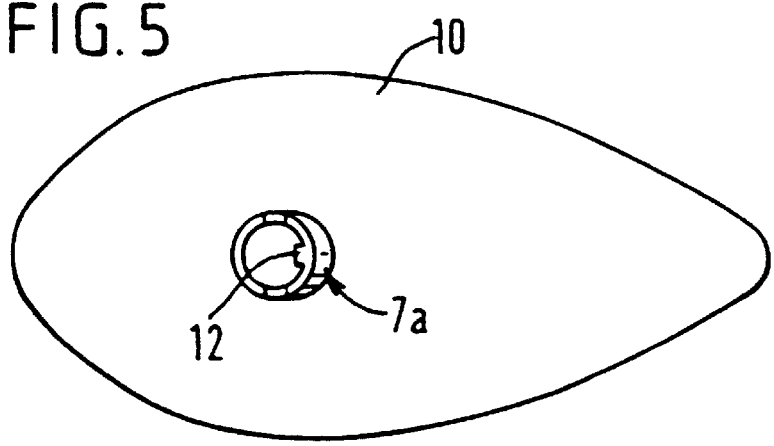

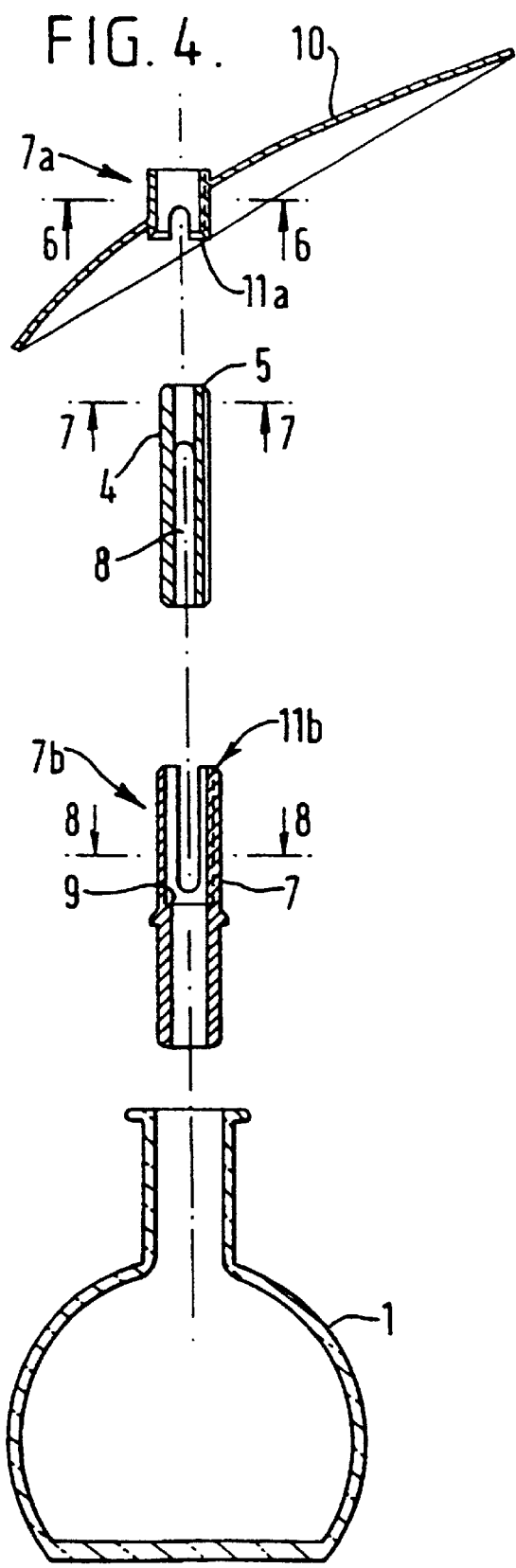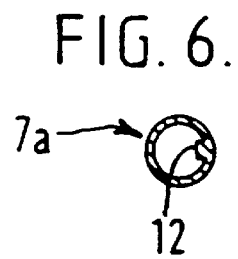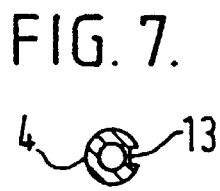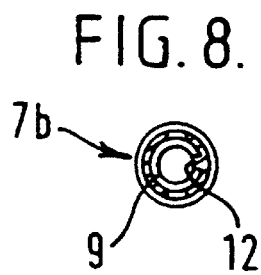

APPARATUS AND METHOD FOR DISSEMINATING AN AIR MODIFYING AGENT

The present invention relates to an apparatus and method for disseminating an air modifying agent into a surrounding atmosphere.

It is known that air modifying agents which vaporise at a relatively low temperature, for example fragrances or incense, can be disseminated into surrounding atmosphere by heating the agent and allowing the vapours thereby created to diffuse away.

In practice, however, the known method has found very limited application. In religious censers, for example, the agent is applied by hand to a heated metal plate, which is time-consuming and labour intensive. Furthermore, the convection currents generated in the air above the plate are of low strength and it is often necessary to swing the censer to achieve effective dissemination of the agent. In the case of scented candles, the agent (scent) is entrained in the fuel (candle wax) for the heat source (candle flame), with the result that much of the agent is combusted in the flame and its effect is lost.

For these reasons, the known systems are not applicable to a wide range of agents and circumstances of use.

The present invention aims to go at least some way towards overcoming the above disadvantages, by providing an improved or at least alternative apparatus and method for disseminating air modifying agents into a surrounding atmosphere.

According to a first aspect of the present invention, therefore, there is provided an apparatus for disseminating an air modifying agent into a surrounding dissolved or intimately admixed) in a flammable liquid carrier which is less volatile than the agent, the apparatus comprising:

(a) reservoir means for holding the flammable liquid carrier;

(b) an igniting station remote from the reservoir means, at which a flame may be created by igniting the flammable liquid carrier;

(c) conveying means (e.g. wick means) for conveying the flammable liquid carrier from the reservoir means to the igniting station;

(d) a vaporisation station spaced from the igniting station and disposed in the path of the flammable liquid carrier, whereby the relatively volatile air modifying agent can be preferentially evaporated away from the flammable liquid carrier prior to combustion of the flammable liquid carrier; and (e) means for heating the flammable liquid carrier in the vaporisation station to assist the preferential evaporation of the air modifying agent at the vaporisation station.

The reservoir means (a) may suitably comprise a conventional bottle, flask or other container. The container may suitably have a neck to which the other parts of the apparatus may be mounted, e.g. releasably mounted. In use, the reservoir means will be substantially air-tight, to prevent evaporation of the flammable liquid carrier from within the reservoir.

It is envisaged that parts (b) to (e) may be provided separately, as a unit, for use with a reservoir means (a) already owned by a user. For example, the first sale to aspect of the present invention as described above. Thereafter, spare parts (b) to (e) may be sold to the user as a unit, for use with the original reservoir means (a), for example if the wick means become inefficient or damaged. It is further possible that the unit of parts (b) to (e) would be fitted into the user's own container (a), which may for example be an old wine bottle or other decorative container.

According to a second aspect of the present invention, therefore, there is provided a device for use with a reservoir means holding a flammable liquid carrier in which an air modifying agent is entrained (e.g dissolved or intimately admixed), to provide the apparatus according to the first aspect of the present invention in which the parts (b) to (e) are releasably mounted to the part (a); the device comprising:

(a') a connector part for connecting the device to the reservoir means;

(b') an igniting station remote from the connector part, at which a flame may be created by igniting the flammable liquid carrier;

(c') conveying means (e.g. wick means) for conveying the flammable liquid carrier from the reservoir means to the igniting station;

(d') a vaporisation station spaced from the igniting station and disposed in the path of the flammable liquid carrier, whereby the relatively volatile air modifying agent can be preferentially evaporated away from the flammable liquid carrier prior to combustion of the flammable liquid carrier; and (e') means for heating the flammable liquid carrier preferential evaporation of the air modifying agent at the vaporisation station.

The apparatus or device according to the present invention may, if desired, be provided in kit form, together with assembly instructions. Such a form of the invention is to be considered as covered by this patent application and subsequent patent (s).

The conveying means (c) or (c') may suitably comprise a conventional wick. The wick may suitably be formed of conventional wick material, e.g. absorbent synthetic and/or natural fibres such as cotton and the like. The fibres will suitably be braided or woven to form an elongate band. A first end of the conveying means contacts the flammable liquid carrier in the reservoir, and a second end contacts the igniting station (b) or (b') at which the flammable liquid carrier is ignited. The thickness of the conveying means will be selected according to the desired rate of dissemination of the air modifying agent, in ways that will be well known to those of ordinary skill in this art.

The igniting station (b) or (b') may suitably comprise a rim region of a conventional metal collar, at which a flame can be created. Where the conveying means (c) or (c') comprises a conventional wick, the metal collar will suitably closely encircle the wick, to prevent the flame travelling back up the wick. Other analogous configurations of igniting station will be well understood by those of ordinary skill in this art.

The vaporisation station (d) or (d') may suitably comprise an aperture or apertures formed through a side wall of the metal collar of the igniting station spaced below the rim of the collar. In this way, a portion of the wick is exposed to the atmosphere before the flammable liquid carrier in the wick reaches the igniting agent can be preferentially evaporated prior to combustion. This significantly restricts the disadvantage mentioned above in connection with the prior art, in which the agent itself was combusted in the flame. The number, size and configuration of the aperture(s) will be selected according to the desired rate of dissemination of the air modifying agent, in ways that will be well known to those of ordinary skill in this art. For example, the aperture(s) can be in the form of elongate slot(s), whereby the wick is exposed to the atmosphere over a longer portion of its length than would be the case if the aperture(s) had been round hole(s); for this reason, it has been found that elongate slot(s) provide a preferred arrangement which leads to efficient dissemination of the air modifying agent into the atmosphere.

Finally, the means (e) or (e') for heating the flammable liquid carrier in the vaporisation station may suitably comprise the side wall of the metal collar itself, provided that the thermal conductivity of the metal is such that sufficient heat is conveyed along the side wall from the rim of the collar (which contacts the flame) to the vaporisation station to effect the required preferential evaporation of the air modifying agent. Correspondingly, it is important that the heat at the vaporisation station should not be enough to cause combustion of the flammable liquid carrier at the vaporisation station. It is also preferred that the heat at the vaporisation station should not be enough to cause undue evaporation of the flammable liquid carrier, as it is clearly undesirable for excessive amounts of uncombusted fuel vapour to be disseminated into the atmosphere.

It is preferred that the metal collar should be somewhat longer than the flame to be created, e.g. between about 1 and 5 times the flame length. The spacing between the (aperture) can then be selected according to the metal used and the nature of the agent and liquid carrier. The metal collar is preferably formed of metal alloy, suitably an aluminium-based alloy or brass. Alternatively, copper can be used.

The means (e) or (e') for heating the flammable liquid carrier in the vaporisation station may take other forms, provided that there is suitably a thermally conductive (e.g. metal) member extending between the flame and the vaporisation station to end there in the vicinity of the flammable liquid carrier. For example, the heating means may take the form of a spring or rod passing inside or outside the wick.

The size of the flame will be selected according to the desired rate of dissemination of the air modifying agent, in ways that will be well known to those of ordinary skill in this art.

A small, household, apparatus according to the present invention may conveniently use a hollow aluminium cylinder of length about 20 to about 50 mm (e.g. about 35–40 mm), external diameter about 6 to about 10 mm (e.g. about 8 mm) and internal diameter about 3 to about mm (e.g. about 4 mm). The aperture(s) preferably take the form of one or more elongate slot about 15 to about 40 mm (e.g. about 25–30 mm) long and about 2 to about 4 mm (e.g. about 3 mm) wide, extending from the end of the collar opposite the igniting station end and terminating more than about 5 mm (e.g. about 9–10 mm) from the igniting station end.

For larger or smaller apparatus, the dimensions will be adjusted accordingly, as will be well understood by those of ordinary skill in this art.

The metal collar forming the igniting and vaporisation stations is suitably connected to the reservoir means by a connector piece, preferably (in the arrangement where the parts (b) to (e) are separable from the part (a)) in the form of a hollow, moulded, heat-resistant plastic support spigot or other tube which is received in the reservoir (e.g. in any neck present) and itself receives and encases the metal collar over a portion of its length. Typically, the rim of the metal collar, defining the igniting station of the apparatus, will project from the support spigot, so that the plastic of the support spigot does not melt under the heat of the igniting station. Such a support spigot constitutes the preferred form of the connector part (a'), referred to above. The heat-resistant plastic may, for example, be polycarbonate, polypropylene or nylon. Such plastics will suitably incorporate a flame retardant.

In use, heat created by the flame at the igniting station is imparted to the metal collar and is conducted along the metal collar by normal thermal conduction. By selecting (in ways which will be well understood by those of ordinary skill in this art) the appropriate materials and configuration of the metal collar and the support spigot (which here will act as an insulating external sleeve for the metal collar), sufficient heat will be conveyed to the vaporisation station to cause the evaporated air modifying agent to be disseminated into the atmosphere at the vaporisation station.

It will be clear that the connector piece (e.g. the support spigot) will be configured so that no part of it obscures the aperture(s) of the vaporisation station. More typically, the support spigot is provided with corresponding aperture(s) in its own side wall, which match with the aperture) of the metal collar when the collar is received in the spigot.

It is most preferred that the apparatus or device further comprises:

(f) deflecting means whereby the flow of evaporated air modifying agent from the vaporisation station is deflected away from the flame at the igniting station.

The deflecting means (f) may suitably comprise a plate member mounted to the apparatus or device (e.g. integrally moulded to the exterior of the support spigot) above the vaporisation station but below the igniting station. The plate extends from the apparatus as a canopy and deflects sideways the upward flow of the (somewhat heated) evaporated air modifying agent.

It is most preferred that the plate member of the deflecting means is inclined at an angle to the vertical, and/or provided with a somewhat concave under surface, whereby a stream of more or less concentrated evaporated air modifying agent can be directed away from the apparatus if desired. The plate member may suitably take the form of a leaf or spoon, with the main parts of the apparatus passing through the plate member, preferably at an angle to the general plane of the plate member.

The method enabled for the first time by the novel apparatus of the present invention is itself new, and constitutes a further feature of the present invention.

According to a third aspect of the present invention, therefore, there is provided a method for disseminating an air modifying agent into a surrounding atmosphere, the method comprising:

(a) entraining (e.g. dissolving or intimately admixing) the air modifying agent in a flammable liquid carrier which is less volatile than the agent;

(b) creating a flame by igniting the flammable liquid carrier;

(c) directing a flow of the flammable liquid carrier, unignited, to a vaporisation station whereby the relatively volatile air modifying agent can be preferentially evaporated away from the flammable liquid carrier prior to combustion of the flammable liquid carrier, and thence directing the flow of the flammable liquid carrier to the flame; and (d) directing heat from the flame to the vaporisation station to heat the flammable liquid carrier in the vaporisation station to assist the preferential vaporisation of the air modifying agent at the vaporisation station.

The above method is preferably performed using an apparatus according to the first aspect of the present invention. In particular, it is most preferred that the method further includes the step of:

(e) deflecting the evaporated air modifying agent away from the flame.

The air modifying agent may be selected from a wide range of agents, such as, for example, insecticides, pesticides, insect repellents, air purifying agents, air freshening agents, fragrances, perfumes, scents etc. The flammable liquid carrier may be selected from a wide range of carriers, such as, for example, oils, hydrocarbon fuels, etc. Paraffin oil is particularly preferred.

The concentration of air modifying agent in the flammable liquid carrier is typically in the range of about 1% to 15% by weight, more preferably about 3% about 10% by weight, e.g. about 5% to about 10% by weight.

As stated above, the relative volatility of the air modifying agent and the flammable liquid carrier must be selected so that the flammable liquid carrier is less volatile than the agent, in order to permit the required evaporation at the vaporisation station of the apparatus. Preferably, the temperature at which substantial evaporation of the air modifying agent occurs is significantly lower (e.g. at least about 30° C. lower, more preferably at least about 50° C. lower, than the flash point of the flammable liquid carrier, and the vaporisation station is heated to a temperature within that differential.

The selection of all the variable factors applicable to this invention can readily be accomplished by those of ordinary skill in this art, taking into account for example the nature of the air modifying agent, the flammable liquid carrier, the desired use of the apparatus, the size, configuration and materials of the apparatus and the size of the flame.

Thus, for example, a typical fragrance (e.g. apple, floral or rose) evaporates substantially at about 50 to about 80° C. The flash point of paraffin oil is about 170 to about 180° C. The apparatus is therefore typically arranged so that the temperature of the vaporisation station in the vicinity of the flammable liquid carrier is in the range of about 50 to about 170° C., more suitably in the range of about 60 to about 130° C., most preferably in the range of about 60 to 90° C.

For ease of understanding the present invention, and to show how the same may be put into effect, an embodiment will now be described, without limitation and purely by way of example, with reference to the accompanying drawings, in which:

FIG. 1 shows in partial vertical cross-section an apparatus for disseminating an air modifying agent into a surrounding atmosphere;

FIG. 2 shows a top view of the apparatus of FIG. 1;

FIG. 3 shows the apparatus of FIG. 1, looking from the left;

FIG. 4 shows in partial vertical cross-section the apparatus of FIG. 1 in exploded form (omitting the wick and the fuel/agent mixture, for clarity);

FIG. 5 shows a bottom view of the deflector part of the apparatus of FIGS. 1 to 4;

FIG. 6 shows a transverse section view taken along the line 6—6 in FIG. 4, looking in the direction of the arrows;

FIG. 7 shows a transverse section view taken along the line 7—7 in FIG. 4, looking in the direction of the arrows; and FIG. 8 shows a transverse section view taken along the line 8—8 in FIG. 4, looking in the direction of the arrows.

Referring to the drawings, there is shown an apparatus for disseminating an air modifying agent into a surrounding atmosphere. The air modifying agent is entrained in a flammable liquid carrier which is less volatile than the agent. A typical system will, for example, be a perfume or fragrance entrained in paraffin oil.

The apparatus comprises reservoir means in the form of a glass or plastic container 1, which holds the paraffin oil and perfume 2; conveying means in the form of a textile wick 3 contacting the paraffin oil/perfume in the container; an elongate metal (e.g. aluminium) alloy collar 4 closely encircling the wick 3 to provide an igniting station at the rim 5 of the collar at which a flame 6 is created by igniting the paraffin oil and a hollow, moulded, heat-resistant plastic support spigot 7 releasably received in a neck of the container 1 and itself receiving and encasing the collar 4 over a portion of its length, the support spigot 7 thus serving as a connector piece to connect the parts together. The heat resistant plastic may be polycarbonate or other plastic such as polypropylene or nylon combined with a flame retardant.

The alloy collar 4 is provided with a pair of diametrically opposed elongate slots 8 (only one shown in the Figures), as is support spigot 7 in the region where it overlies the slots in the collar. In this way, a vaporisation station is provided, spaced below the igniting station, at which the wick 3 is exposed to the surrounding atmosphere. The effect of this is that the vaporisation station lies in the path of the unignited paraffin oil/perfume as it travels up the wick 3. The relatively volatile perfume can thus preferentially evaporate away from the paraffin oil prior to combustion of the paraffin oil at the igniting station.

The alloy collar 4 contacts the flame 6 at the collar's rim 5. In this way, heat is conveyed along the collar to the vaporisation station, thereby heating the paraffin oil in the vaporisation station, to assist the preferential evaporation of the perfume as mentioned above.

The support spigot 7 encases the collar 4 over only a portion of the length of the support spigot. In the region of the collar's rim 5, the support spigot is shorter than the collar so that the rim 5 of the collar projects a short way from the end of the spigot (e.g. about 3 mm). In this way, the plastic spigot is not melted by the heat at the igniting station. At the other end of the collar, nearer the container 1, the collar rests on an internal abutment 9 of the spigot, below the slots 8. The wall of the support spigot 7 is provided with slots corresponding generally in size and location to the slots 8 of the metal collar. In this way, the wick 3 lying beside the slots 8 is exposed to the surrounding atmosphere through the walls of the metal collar 4 and the support spigot 7.

The apparatus is further provided with deflecting means in the form of a deflector plate 10, whereby the flow of (somewhat heated) evaporated perfume from the slots 8 is deflected away from the flame 6, to prevent or restrict combustion of the perfume vapour by the flame.

In more detail, the support spigot 7 is formed as two separable parts 7*a*, 7*b*, an upper one of which 7*a* rests in use on a lower 7*b* and is seated thereon by conventional internal cooperating abutments 11*a*, 11*b*. The upper part 7*a* of the support spigot is integrally moulded with the deflector plate as a unit, and the parts of the whole assembly, i.e. the spigot parts 7*a*, 7*b* and metal collar 4, are maintained in mutual alignment via a conventional keying pair of a longitudinal ridge 12 and slot 13.

The deflector plate 10 extends from the apparatus as a canopy and deflects sideways the upwards flow of evaporated perfume emerging from the slots 8 at the vaporisation station. The deflector plate 10 is inclined at an angle to the vertical and has a somewhat concave under surface. In this way, the apparatus has an attractive appearance and a rather concentrated stream of perfume vapour is directed away from the flame 6, to the right as shown in FIG. 1 (see arrow A).

The manufacture, assembly and disassembly of the parts of the apparatus is very straightforward, as will be clear to those of ordinary skill in this art. To operate the apparatus, and thereby to perform the method of the present invention, it is merely necessary to ensure that sufficient wick 3 is present at the rim 5 of the metal alloy collar 4 to create the flame 6. By lighting the wick and creating the flame 6, the paraffin oil is drawn out of the reservoir container 1 up the wick, bringing with it the perfume to the slots 8 at the vaporisation station. After an initial warming up time, the alloy collar 4 is sufficiently heated by the flame that the perfume readily evaporates through the slots 8, from where it is disseminated effectively into the surrounding atmosphere, under the effects of the heating and the deflector plate 10.

The foregoing broadly describes the present invention without limitation to specific embodiments. Variations and modifications as will be readily apparent to those of ordinary skill in this art are intended, and will be understood, to be included within the scope of this application and resulting patent(s).

I claim:

1. An apparatus for disseminating an air modifying agent into a surrounding atmosphere, the air modifying agent being entrained in a flammable liquid carrier which is less volatile than the agent, the apparatus comprising:
    a) a reservoir means for holding the flammable liquid carrier;
    b) an igniting station remote from the reservoir means, at which a flame may be created by igniting the flammable liquid carrier;
    conveying means for conveying the flammable liquid carrier from the reservoir means to the igniting station;
    d) a vaporization station external to said reservoir means spaced from the igniting station and disposed in the path of the flammable liquid carrier, whereby the relatively volatile air modifying agent is preferentially evaporated away from the flammable liquid carrier prior to combustion of the flammable liquid carrier; and
    e) means for heating the flammable liquid carrier in the vaporization station to assist the preferential evaporation of the air modifying agent at the vaporization station.

2. An apparatus according to claim 1, wherein the reservoir means (a) comprises a bottle or flask.

3. An apparatus according to claim 2, wherein the reservoir means (a) has a neck to which the other parts of the apparatus may be mounted.

4. An apparatus according to claim 3, wherein the reservoir means is substantially air-tight in use.

5. An apparatus according to claim 1, wherein the conveying means (c) comprises a wick.

6. An apparatus according to claim 1, wherein the igniting station (b) comprises a rim region of a collar for the conveying means (c) or at which a flame can be created.

7. An apparatus according to claim 6, wherein the collar is metal.

8. An apparatus according to claim 7, wherein the vaporisation station (d) comprises an aperture or apertures provided in a side wall of the collar of the igniting station spaced below the rim of the collar.

9. An apparatus according to claim 8, wherein the means (e) for heating the flammable liquid carrier in the vaporisation station comprises a thermally conductive member having a first end, wherein when the flame has been created by igniting the flammable liquid carrier, in contact with the flame and a second end in contact with the flammable liquid carrier at the vaporisation station, the thermal conductivity of the member being such that sufficient heat is conveyed along the member from the flame to the vaporisation station to effect preferential evaporation of the air modifying agent while not causing combustion of the flammable liquid carrier at the vaporisation station.

10. An apparatus according to claim 9, wherein the collar of the igniting station (b) is thermally conductive and the thermally conductive member comprises the side wall of the collar.

11. An apparatus according to claim 9, wherein the thermally conductive member comprises a spring or rod passing inside or outside the conveying means (c).

12. An apparatus according to claim 11, wherein the thermally conductive member is metal.

13. An apparatus according to claim 12, wherein there is further provided
    f) deflecting means whereby the flow of evaporated air modifying agent from the vaporisation station is deflected away from the flame at the igniting station.

14. A device for use with a reservoir means (a) holding a flammable liquid carrier in which an air modifying agent is entrained, to provide an apparatus wherein the apparatus is an apparatus for disseminating an air modifying agent into a surrounding atmosphere, the air modifying agent being entrained in a flammable liquid carrier which is less volatile than the agent, the device comprising:
    a') a connector part for connecting the device to the reservoir means;
    b) an igniting station remote from the reservoir means, at which a flame may be created by igniting the flammable liquid carrier;
    c) conveying means for conveying the flammable liquid carrier from the reservoir means to an igniting station;
    d) a vaporization station external to said reservoir means and spaced from the igniting station and disposed in the path of the flammable liquid carrier, whereby the relatively volatile air modifying agent is evaporated away from the flammable liquid carrier prior to combustion of the flammable liquid carrier; and
    e) means for heating the flammable liquid carrier in the vaporization station to assist the preferential evaporation of the air modifying agent at the vaporization station; in which the parts (b) to (e) are releasably mountable to the reservoir means (a) by the part (a') to provide said apparatus.

15. A device according to claim 14, wherein the reservoir means (a) comprises a bottle or flask.

16. A device according to claim 15, wherein the reservoir means (a) has a neck to which the other parts of the apparatus may be mounted.

17. A device according to claim 16, wherein the reservoir means is substantially air-tight in use.

18. A device according to claim 14, wherein the conveying means comprises a wick.

19. A device according to claim 14, wherein the igniting station comprises a rim region of a collar for the conveying means at which a flame can be created.

20. A device according to claim 19, wherein the collar is metal.

21. A device according to claim 20, wherein the vaporisation station comprises an aperture or apertures provided in a side wall of the collar of the igniting station spaced below the rim of the collar.

22. A device according to claim 21, wherein the means for heating the flammable liquid carrier in the vaporisation station comprises a thermally conductive member having a first end in contact with the flame and a second end in contact with the flammable liquid carrier at the vaporisation station, the thermal conductivity of the member being such that sufficient heat is conveyed along the member from the flame to the vaporisation station to effect preferential evaporation of the air modifying agent while not causing combustion of the flammable liquid carrier at the vaporisation station.

23. A device according to claim 22, wherein the collar of the igniting station is thermally conductive and the thermally conductive member comprises the side wall of the collar.

24. A device according to claim 22, wherein the thermally conductive member comprises a spring or rod passing inside or outside the conveying means.

25. A device according to claim 24, wherein the thermally conductive member is metal.

26. A device according to claim 14, wherein the connector piece comprises a hollow heat-resistant support tube which is received in a neck of the reservoir.

27. A device according to claim 26, wherein the igniting station comprises a rim region of a collar for the conveying means and the support tube receives and encases the collar over a portion of the length of the collar.

28. A device according to claim 27, wherein there is further provided
 f) deflecting means whereby the flow of evaporated air modifying agent from the vaporisation station is deflected away from the flame at the igniting station.

29. A device according to claim 28, wherein the deflecting means (f) comprises a plate member mounted to the apparatus or device above the vaporisation station but below the igniting station, the plate member extending from the apparatus or device as a canopy for deflecting sideways the upward flow of the heated, evaporated, air modifying agent.

30. A device according to claim 29, wherein the plate member is inclined at an angle to the vertical and/or is provided with a concave under surface, whereby a stream of evaporated air modifying agent can be directed away from the apparatus.

31. A method for disseminating an air modifying agent into a surrounding atmosphere, the method comprising:
 a) entraining the air modifying agent in a flammable liquid carrier which is less volatile than the agent;
 b) creating a flame by igniting the flammable liquid carrier;
 c) directing a flow of the flammable liquid carrier, unignited, to an external station whereby the relatively volatile air modifying agent is preferentially evaporated away from the flammable liquid carrier prior to combustion of the flammable liquid carrier, and thence directing the flow of the flammable liquid carrier to the flame; and
 d) directing heat from the flame to the external vaporization station to heat the flammable liquid carrier in the external vaporization station to assist the preferential vaporization of the air modifying agent at the external vaporization station.

32. The method according to claim 31, further including the step of:
 e) deflecting the evaporated air modifying agent away from the flame.

33. An apparatus for disseminating an air modifying agent into a surrounding atmosphere, the air modifying agent being entrained in a flammable liquid carrier which is less volatile than the agent, the apparatus comprising:
 a) a reservoir means for holding the flammable liquid carrier;
 b) an igniting station remote from the reservoir means, at which a flame may be created by igniting the flammable liquid carrier;
 c) conveying means for conveying the flammable liquid carrier from the reservoir means to the igniting station;
 d) a vaporization station external to said reservoir means spaced from the igniting station and disposed in the path of the flammable liquid carrier, whereby the relatively volatile air modifying agent is evaporated away from the flammable liquid carrier prior to combustion of the flammable liquid carrier; and
 (e) means configured to draw heat from said igniting station for heating the flammable liquid carrier in the vaporization station to assist the preferential evaporation of the air modifying agent at the vaporization station.

* * * * *

UNITED STATES PATENT AND TRADEMARK OFFICE
CERTIFICATE OF CORRECTION

PATENT NO.   : 6,562,294 B1
DATED        : May 13, 2003
INVENTOR(S)  : Nigel Peter Smith It is certified that error appears in the above-identified patent and that said Letters Patent is hereby corrected as shown below:

<u>Title page,</u>
Insert item:
-- Related U.S. Application Data

(63)   Continuation of Application No. PCT/GB98/03194, filed October 26, 1998 --

Signed and Sealed this

Ninth Day of March, 2004

JON W. DUDAS
*Acting Director of the United States Patent and Trademark Office*